United States Patent [19]

Colvin

[11] Patent Number: 4,920,978
[45] Date of Patent: May 1, 1990

[54] METHOD AND APPARATUS FOR THE ENDOSCOPIC TREATMENT OF DEEP TUMORS USING RF HYPERTHERMIA

[75] Inventor: David P. Colvin, Apex, N.C.

[73] Assignee: Triangle Research and Development Corporation, Raleigh, N.C.

[21] Appl. No.: 238,824

[22] Filed: Aug. 31, 1988

[51] Int. Cl.$^5$ .......................... A61N 1/05; A61N 1/06
[52] U.S. Cl. .................................... 128/784; 128/736; 128/804
[58] Field of Search .................... 128/303.15, 784, 785, 128/786, 787, 804, 736

[56] References Cited

U.S. PATENT DOCUMENTS

| | | | |
|---|---|---|---|
| 3,901,242 | 8/1975 | Storz | 128/303.15 |
| 4,016,886 | 4/1977 | Doss et al. | 128/804 X |
| 4,116,198 | 9/1978 | Roos | 128/303.15 |
| 4,170,234 | 10/1979 | Graham | 128/303.14 |
| 4,374,517 | 2/1983 | Hagiwara | 128/6 |
| 4,494,539 | 1/1985 | Zenitani et al. | 128/303.1 |
| 4,517,976 | 5/1985 | Murakoshi et al. | 128/303.15 |
| 4,531,524 | 7/1985 | Mioduski | 128/804 X |
| 4,557,272 | 12/1985 | Carr | 128/804 X |
| 4,559,943 | 12/1985 | Bowers | 128/303.14 |
| 4,572,214 | 2/1986 | Nordenstrom et al. | 128/785 |
| 4,643,187 | 2/1987 | Okada | 128/303.15 |
| 4,708,137 | 11/1987 | Tsukagoshi | 128/303.5 |
| 4,716,897 | 1/1988 | Noguchi et al. | 128/303.15 |

FOREIGN PATENT DOCUMENTS 0227324 9/1985 Fed. Rep. of Germany ........................ 128/303.15

Primary Examiner—Lee S. Cohen
Attorney, Agent, or Firm—Robert G. Rosenthal

[57] ABSTRACT

An attachment for an endoscope for the treatment of deep tissue tumors using RF hyperthermia is disclosed. In one embodiment, electrodes are adapted to straddle or penetrate a tumor in order to confine the interstitial current heating and are detachably fitted to the distal end of the endoscope. The electrodes are electrically coupled to an RF generating power source by means of wires that extend along the outer surface of the tubular body of the endoscope and are detachably mounted thereto.

14 Claims, 5 Drawing Sheets

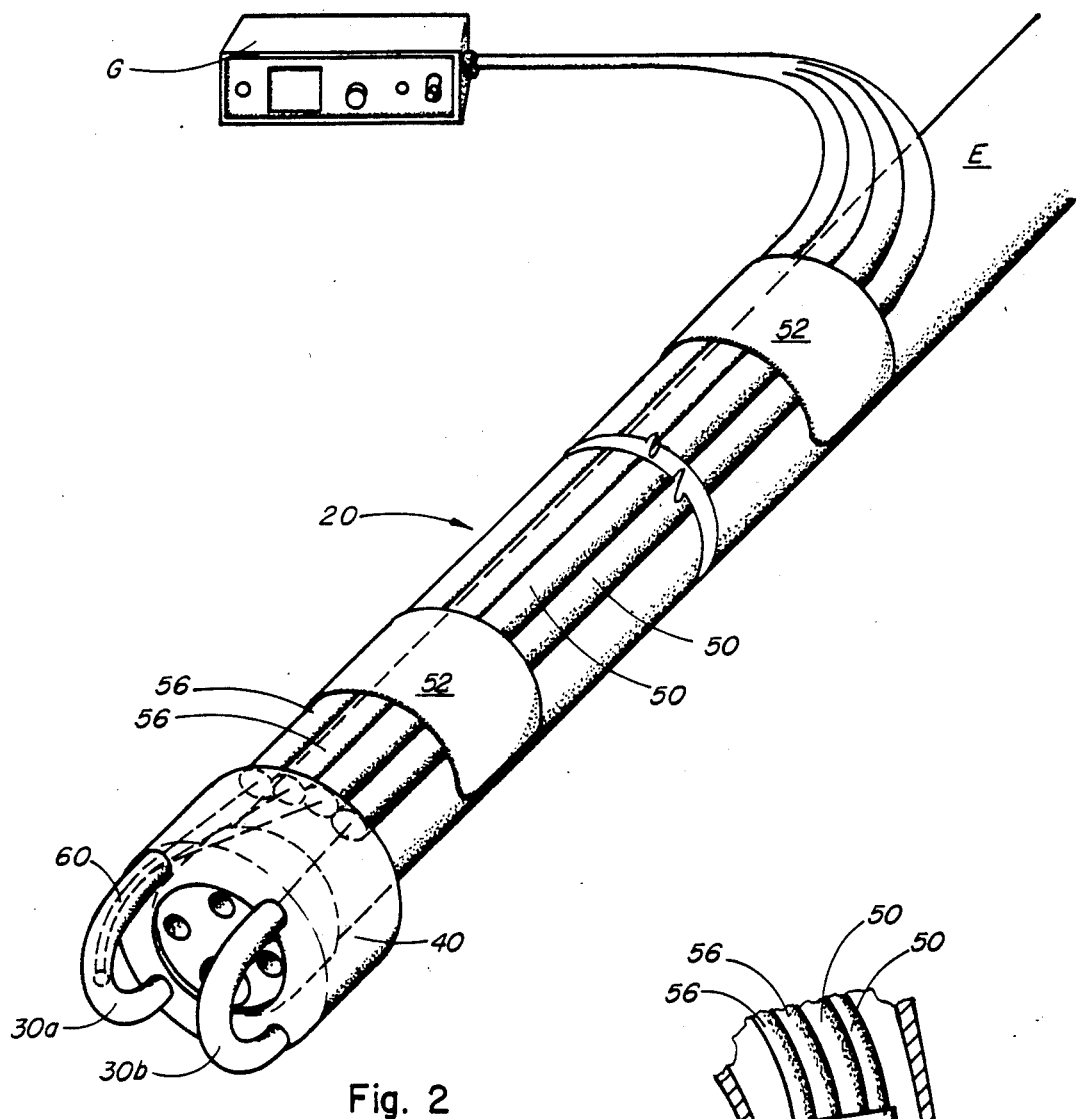
Fig. 2
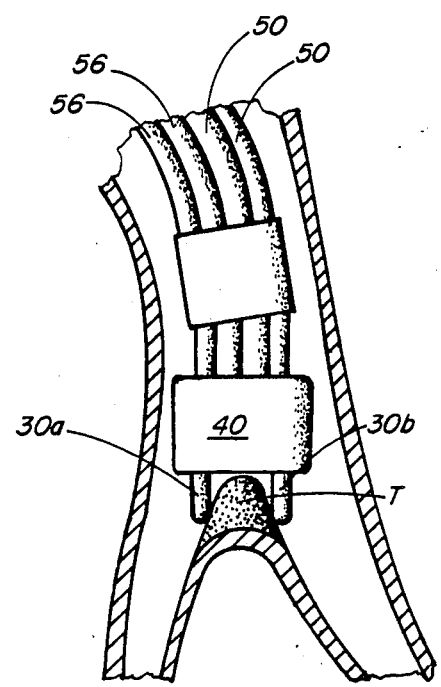
Fig. 4
Fig. 5

METHOD AND APPARATUS FOR THE ENDOSCOPIC TREATMENT OF DEEP TUMORS USING RF HYPERTHERMIA

This invention was made with partial Government support under SBIR contract No. N93-CM-67951 awarded by the Division of Health and Human Services/National Cancer Institute. The Government may have certain rights in this invention.

FIELD OF THE INVENTION

This invention relates generally to the treatment of deep tumors and more specifically to the treatment of deep tumors using endoscopically applied RF energy to induce hyperthermia.

BACKGROUND OF THE INVENTION

The use of RF energy in the medical field is known. For example U.S. Pat. No. 4,716,897 to Noguchi et al. discloses an electrosurgical apparatus that includes a radio frequency (RF) power source for supplying an object to be cauterized through a treatment tool and an electrode plate.

In addition, hyperthermia has been applied with increasing success for therapy of malignant tumors, both as an adjuvant to ionizing radiation and chemotherapy and also as a singular modality in which tissue temperatures are elevated sufficiently to produce cellular death. In both cases, it is desireable to induce a state of hyperthermia that is localized by interstitial current heating to a specific area while concurrently insuring minimum thermal damage to healthy surrounding tissue. Often, the tumor is located subcutaneously and its healing requires either surgery, endoscopy procedures or external radiation. However, externally inducing a state of hyperthermia in deep body tissue is difficult to accomplish because the current density is diluted due to its absorption by healthy tissue. In addition, a portion of the RF energy is reflected at the muscle/fat and bone interfaces which adds to the problem of depositing a known quantity of energy directly on a small tumor. Similarly, it is known to use microwave antenna catheters inserted through endoscopes to irradiate tumors. However, this method is not without its drawbacks since the microwave catheter acts as an antenna wherein the energy radiates in all directions and the amount of energy reaching the tumor is difficult to determine with precision. The measurement of the amount of energy reaching the tumor becomes important because the rate of tissue damage increases as an exponential function of absolute temperature and the cummulative injury accrues linearly with time. In addition, the period of time that the surgeon can remain within the body is limited and microwave deposition of energy requires the antenna to be present within the body for an extended period of time.

It is, therefore, an object of the present invention to provide an effective treatment for deep tumors using an endoscope.

It is another object of the present invention to provide an effective treatment for deep tumors that uses RF energy to deposit a known quantity of energy on the tumor.

It is still another object of the present invention to provide an effective treatment for deep tumors that minimizes the damage to the surrounding healthy tissue.

It is a further object of the invention to provide an effective treatment for deep tumors that minimizes the invasiveness of the therapy.

It is yet another object of the present invention to treat the tumor using RF energy to quickly elevate the temperature of the tumor to a predetermined level.

SUMMARY OF THE INVENTION

To accomplish the objects described above, there is provided an attachment for conventional endoscopes that is adapted to produce RF hyperthermia in tumors. A conventional endoscope has a cylindrical body with a proximal end and a distal end. An electrode means is adapted to deliver interstitial electrical energy to the tumor and is connected to a means for mounting the electrode means proximate to the distal end of the endoscope. A means adapted to deliver electrical energy to the electrode means is connected to the electrode means and is connected to the body of the endoscope.

BRIEF DESCRIPTION OF THE DRAWINGS

Some of the features and advantages of the invention having briefly been stated, others will appear from the detailed description which follows, when taken in connection with the accompanying drawings, in which

FIG. 2 is a perspective view of an endoscope equipped with the RF hyperthermia attachment of the present invention.

FIG. 4 is an end view of an endoscope equipped with the RF hyperthermia unit of the present invention.

FIG. 5 is a schematic view of a portion of a lung having a tumor and being straddled by th electrodes of the RF hyperthermia attachment of the present invention.

DETAILED DESCRIPTION OF THE ILLUSTRATED EMBODIMENTS

While the present invention will be described more fully hereinafter with reference to the accompanying drawings, in which a particular embodiment is shown, it is to be understood at the outset that persons skilled in the art may modify the invention herein described while still achieving the favorable results of this invention. Accordingly, the description which follows is to be understood as a broad teaching disclosure directed to persons of skill in the appropriate arts and not as limiting upon the present invention.

Figure 1:
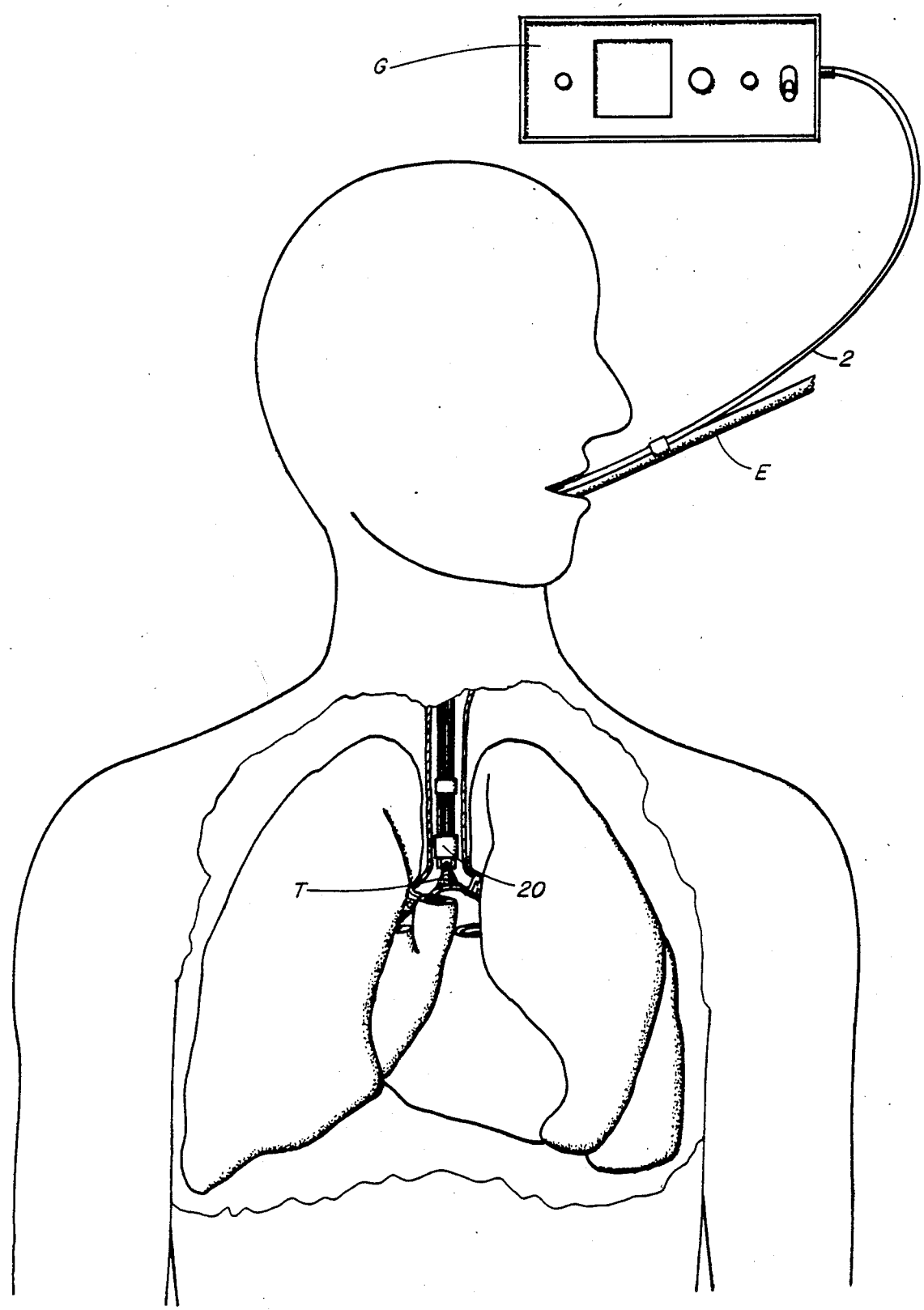
FIG. 1 is a schematic view of a patient, partially broken away and showing a lung having a tumor being treated by the RF hyperthermia unit of the present invention.
Figure 3:
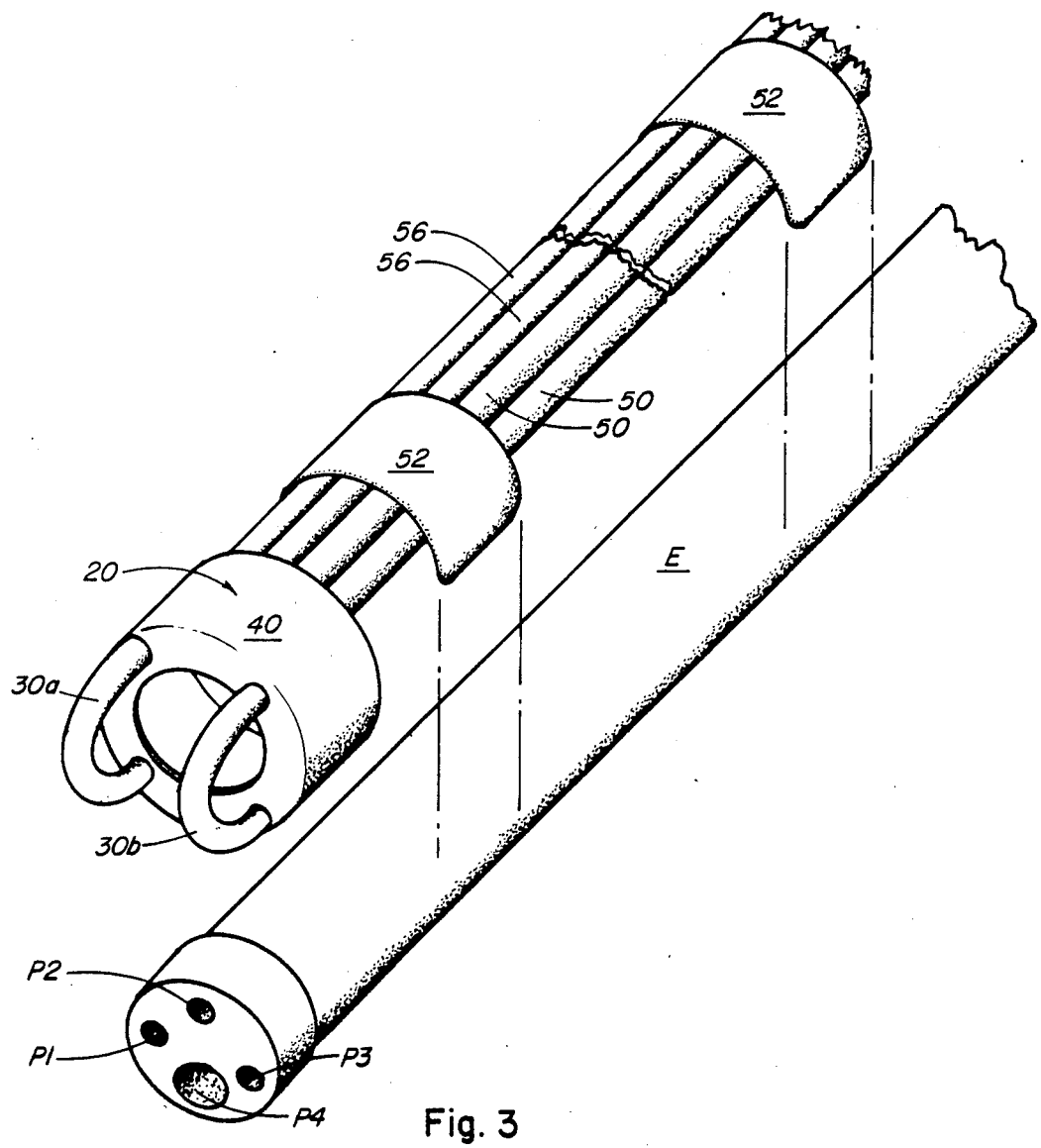
FIG. 3 is an exploded view, taken in perspective of an endoscope equipped with the RF hyperthermia attachment of the present invention.
Figure 6:
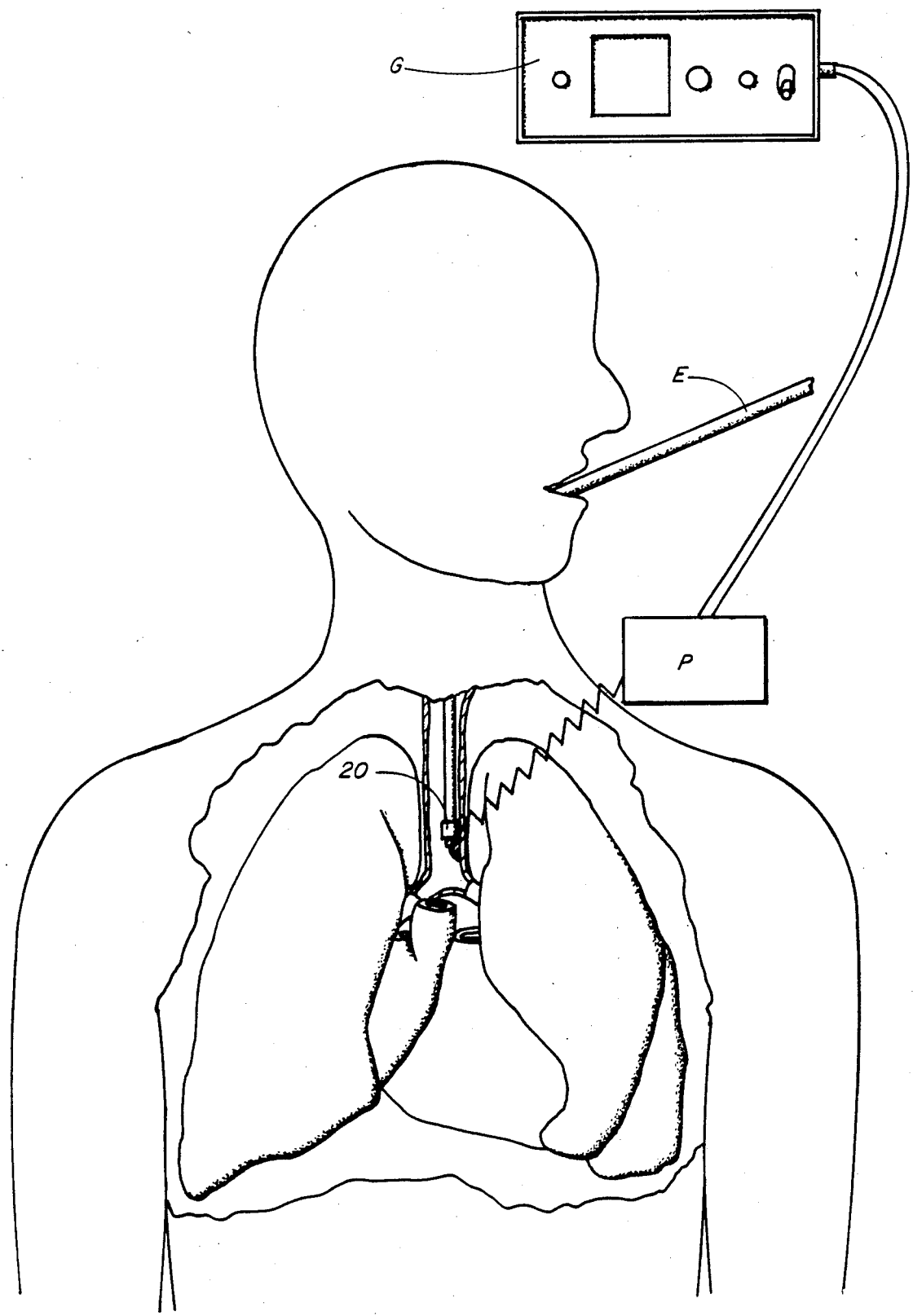
FIG. 6 is a schematic view of a patient, partially broken away and showing a lung having a tumor being treated by an alternate, embodiment of the RF hyperthermia attachment of the present invention utilizing an electrode adapted to be passed within the port of the endoscope and an external plate which acts as the receiving electrode.
Figure 7:
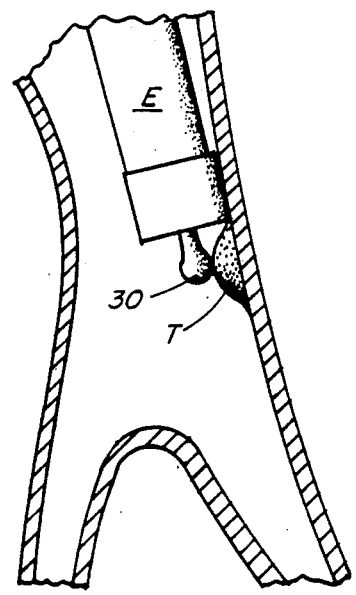
FIG. 7 is a schematic view of a portion of a lung having a tumor located on the side wall of the bronchial passageway and being contacted by the electrode of the RF hyperthermia attachment of the present invention.

Referring more specifically to the drawings, and particularly to FIG. 1, a patient having a cancerous tumor T located in the bronchial passageway is there illustrated. As is known to persons skilled in the art, endoscopes are commonly inserted into the body passageways, such as the lungs, intestines and the urinary tract for a variety of diagnostic and treatment purposes. The endoscope commonly includes a plurality of pathways P1, P2, P3 which extend along its length from its proximal end to its distal end and which may include a light source, viewing optics as well as a port P4 for the introduction of a variety of treatment/diagnostic devices such as forceps, biopsy needles and the like. For the sake of clarity, the discussion which follows is limited to use of the present invention in a lung endoscope, however, it will be noted that the invention may easily be applied with equal efficacy to the colon, male and female reproductive organs and the gastrointestinal tract.

As shown in FIG. 1, the endoscope E has been inserted in the patient's mouth and extends down the trachea and into the bronchial passageway. The RF hyperthermia attachment of the present invention, generally indicated at 20 is connected to the endoscope E. The RF hyperthermia attachment 20 is connected to a control unit G which may also include the RF generator, a temperature sensing and readout apparatus and a feedback loop, as will be explained hereinbelow in greater detail.

In the model that was constructed as a 2 megahertz generator was used to produce temperature at the electrodes ranging from 35 degrees centigrade to 60 degrees centigrade. The 2 megahertz frequency produces no electrical shock and minimizes electromagnetic perturbations of the control sensor.

The RF hyperthermia attachment comprises an electrode means, a means for mounting the electrode means to the distal end of the endoscope and a means for delivering electrical energy from the control unit G to the electrode means. In another embodiment of the invention, a temperature sensing means is also included.

The electrode means of the present invention comprises a pair of small, curved, dipole electrodes 30a, 30b which form a bipolar probe that can be used to straddle small tumors such as is shown in FIG. 5.

The means for mounting the electrodes comprises a circular collar 40 that is adapted to be detachably fitted to the distal end of the endoscope by means of a pressure fit. The central portion of the collar 40 is open so that when it is attached to the distal end of the endoscope, the functionality of the bronchoscope optics, light sources and access port remains unimpaired.

The attachment also includes a means for delivering electrical energy to the electrodes from control unit. As shown in FIG. 2 through 5, a series of small gauge wires 50 are adapted to be mounted to the exterior of the endoscope body. They are maintained in contact with the exterior of the endoscope body in essentially flat position by means of a series of spaced apart clips 52.

In an additional aspect of the invention, a thermistor means or similar temperature sensing device 60 is embedded within at least one of the electrodes 30. The thermistor is connected by means of wire 56 to the control unit. The generator is equipped with a conventional closed loop feedback system which enables the temperature at the electrode to be controlled with precision. As a result, precise quantities of RF thermal energy can be delivered to the tumor to be destroyed thus, enhancing the efficacy of the treatment to heretofore unachievable levels.

In operation, the collar 40 is slipped on to the distal end of the endoscope E. The wires 50, 56 are similarly connected to the endoscope by means of clips 52 and have one of their ends connected to the respective electrodes and thermistor, respectively, and the opposite ends connected to the control unit. The physician then inserts the endoscope, attached to the RF hyperthermia unit, into the lung in the conventional manner using the internal optics and light source until the electrodes straddle the tumor as shown in FIG. 5. The tumor is then heated to an elevated temperature such as 48 degrees centigrade for one minute or to 50 degrees for 30 seconds after which the endoscope is removed.

Figure 8:
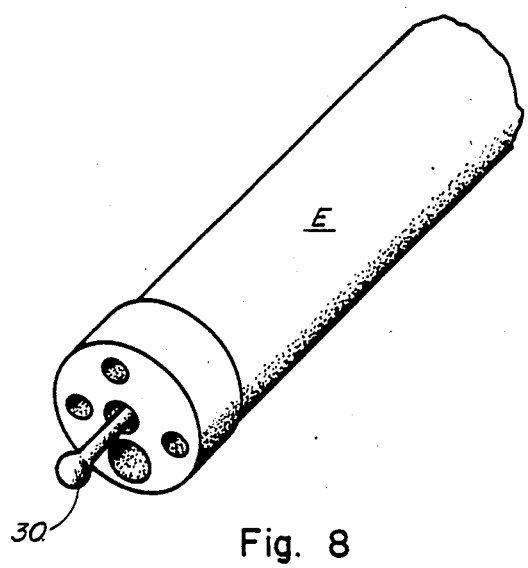
FIG. 8 is a perspective view of the distal portion of an endoscope showing the single electrode of the RF hyperthermia attachment extending outwardly from the distal end of the endoscope.
Figure 9A:
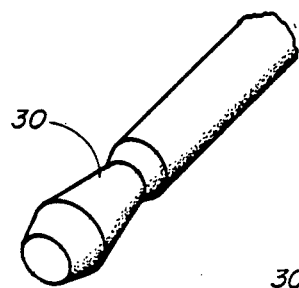
FIGS. 9a and 9b are perspective views of alternate embodiments of the electrodes.
Figure 9B:
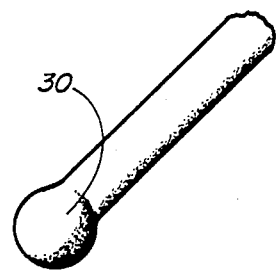
Figure 10:
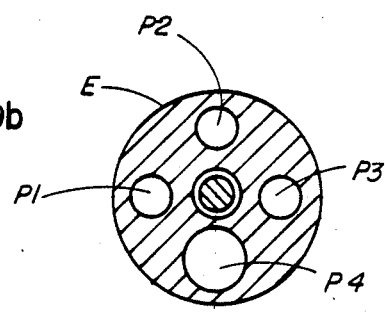
FIG. 10 is an end view of the distal end of an endoscope showing the electrode of the RF hyperthermia attachment of the present invention therein.

In another embodiment of the invention shown in FIGS. 6 through 10, the tumor to be treated is positioned in the lung so that it cannot be straddled by the electrodes. In this case, a single electrode is inserted into the access port of the endoscope (as best shown in FIG. 8) so as to be in direct contact with the tumor. An electrical ground plate P is then placed externally in electrical contact with the patient. Thus, when the apparatus is activated as described above, a known quantity of RF energy of known and high current density is applied directly to the tumor thus yielding a predictable path for current to flow through the tumor and into plate P thus enabling a known amount of energy to be deposited in a known volume of tissue. Exemplary electrode shapes are shown in FIGS. 9a and 9b.

The foregoing embodiments and examples are to be considered illustrative, rather than restrictive of the invention, and those modifications which come within the meaning and range of equivalence of the claims are to be included therein.

That which is claimed is:

1. An RF hyperthermia attachment for adapting endoscopes having an elongated tubular body with a proximal end and a distal end for quickly treating deep body cancerous tumors by delivering RF energy generated by a control unit thereto, said RF hyperthermia attachment comprising:
   electrode means adapted to deliver electrical energy interstitially to the tumor,
   means connected to said electrode means for detachably mounting said electrode means to the distal end of the endoscope,
   means connected to said electrode means adapted to deliver electrical energy thereto and being adapted to be connected to the body of the endoscope, and wherein said means for delivering electrical energy to the electrode means is adapted to be detachably mounted to the external surface of the body of the endoscope.

2. An apparatus according to claim 1 wherein said electrode means comprises a positive and a negative electrode.

3. An apparatus according to claim 2 wherein said positive and negative electrodes comprise a pair of spread apart dipole electrodes adapted to straddle a tumor.

4. An apparatus according to claim 1 wherein said means for mounting said electrode means comprises a collar adapted to be detachably fitted to the distal end of the endoscope.

5. An RF hyperthermia attachment for adapting endoscopes having an elongated tubular body with a proximal end and a distal end for quickly treating deep body cancerous tumors by delivering RF energy generated by a control unit thereto, said RF hyperthermia attachment comprising:

a pair of dipole electrodes adapted to deliver electrical energy interstitially to the tumor;

means connected to said dipole electrodes for detachably fitting said dipole electrodes to the external surface of the distal end of the endoscope; and means connected to the dipole electrodes adapted to deliver electrical energy thereto and being adapted to be connected to the body of the endoscope; and thermistor means for measuring the RF hyperthermia induced temperature proximate the tumor, whereby the temperature of the tumor can be carefully and closely controlled.

6. An RF hyperthermia attachment for adapting endoscopes having an elongated tubular body with a proximal end and a distal end for quickly treating deep body cancerous tumors by delivering RF energy generated by a control unit thereto, said RF hyperthermia attachment comprising:

electrode means adapted to deliver electrical energy interstitially to the tumor, means connected to said electrode means for detachably mounting said electrode means to the distal end of the endoscope, means connected to said electrode means adapted to deliver electrical energy thereto and being adapted to be connected to the body of the endoscope, and thermistor means for measuring the RF hyperthermia induced temperature proximate the tumor and for transmitting a signal representative of the temperature to a control unit.

7. An apparatus according to claim 6 wherein said electrode means comprises a positive and a negative electrode.

8. An apparatus according to claim 7 wherein said positive and negative electrodes comprise a pair of spaced apart dipole electrodes adapted to straddle a tumor.

9. An apparatus according to claim 6 wherein said attachment includes a closed loop feedback circuit that employs said signal representative of the temperature to precisely measure and control the temperature of said electrode means.

10. A method of treating deep tissue tumors using RF hyperthermia administered with an endoscope of the type adapted to be inserted into a body cavity having an elongated tubular body, a proximal end and a distal end and wherein an electrode adapted to deliver electrical energy to the tumor is connected proximate the distal end of the endoscope and wherein wires connect the electrode to a power source and a control unit comprising the steps of:

inserting the endoscope including the electrode and the wires into the body cavity, positioning the electrode in contacting relation with the tumor to be treated, transferring electrical energy from the electrode into the tumor for a predetermined period of time, measuring the temperature proximate the electrode during treatment.

11. The method according to claim 10 wherein the tumor is heated to a temperature of approximately 48 degrees centigrade and is maintained at that temperature for approximately one minute.

12. The method of claim 10 wherein the tumor is heated to a temperature of approximately 50 degrees centigrade and is maintained at that temperature for approximately 30 seconds.

13. The method according to claim 10 further including the step of feeding back to the control unit a signal representative of the temperature of the electrode.

14. The method according to claim 13 further including the step of utilizing the signal representative of the electrode temperature in a closed loop feedback circuit to precisely measure and control the electrode temperature.

* * * * *